(12) United States Patent
Dechev et al.

(10) Patent No.: US 12,399,168 B2
(45) Date of Patent: Aug. 26, 2025

(54) URINALYSIS TEST STRIP FOR OVER-THE-COUNTER USE

(71) Applicant: YOUCOUNT INC., Vancouver (CA)

(72) Inventors: Teodora Dechev, West Vancouver (CA); Nikolai Dechev, Victoria (CA); Ian Fraser, Victoria (CA)

(73) Assignee: YOUCOUNT INC., Vancouver (CA)

( * ) Notice: Subject to any disclaimer, the term of this patent is extended or adjusted under 35 U.S.C. 154(b) by 821 days.

(21) Appl. No.: 17/627,649

(22) PCT Filed: Jul. 15, 2020

(86) PCT No.: PCT/CA2020/050985
§ 371 (c)(1),
(2) Date: Jan. 15, 2022

(87) PCT Pub. No.: WO2021/007671
PCT Pub. Date: Jan. 21, 2021

(65) Prior Publication Data
US 2022/0276228 A1   Sep. 1, 2022

(30) Foreign Application Priority Data
Jul. 15, 2019   (CA) ................................ CA 3049972

(51) Int. Cl.
*G01N 33/00*   (2006.01)
*C12Q 1/48*   (2006.01)
(Continued)

(52) U.S. Cl.
CPC ........... *G01N 33/521* (2013.01); *C12Q 1/485* (2013.01); *G01N 33/54388* (2021.08);
(Continued)

(58) Field of Classification Search
CPC .................................................... G01N 33/521
(Continued)

(56) References Cited

U.S. PATENT DOCUMENTS

| 4,125,372 A | 11/1978 | Kawai et al. |
| 4,755,058 A | 7/1988 | Shaffer |

(Continued)

FOREIGN PATENT DOCUMENTS

| EP | 437254 B1 | 12/1995 |
| GB | 2339615 B | 2/2001 |

(Continued)

OTHER PUBLICATIONS

International Search Report from the ISA for International Patent App. No. PCT/CA2020/050985, mailed Nov. 9, 2020, 8 pages.
(Continued)

*Primary Examiner* — Elizabeth A Robinson
*Assistant Examiner* — Emily R. Berkeley (57) ABSTRACT

A test strip for urinalysis is provided, the test strip including a reagent pad for detecting a concentration of a selected analyte, the reagent pad attached to the test strip and comprising a substrate and an analyte detection system retained thereon, the analyte detection system including a plurality of components necessary for detection of the selected analyte, wherein at least one of the plurality of components is a variable component, the variable component immobilized on the substrate at a plurality of amounts on the reagent pad.

33 Claims, 3 Drawing Sheets

(51) Int. Cl.

| | | |
|---|---|---|
| *G01N 33/52* | (2006.01) | |
| *G01N 33/543* | (2006.01) | |
| *G01N 33/569* | (2006.01) | |
| *G01N 33/66* | (2006.01) | |
| *G01N 33/68* | (2006.01) | |
| *G01N 33/70* | (2006.01) | |
| *G01N 33/74* | (2006.01) | |
| *G01N 33/84* | (2006.01) | |
| *G01N 33/94* | (2006.01) | |

(52) U.S. Cl.
CPC ....... *G01N 33/56972* (2013.01); *G01N 33/66* (2013.01); *G01N 33/6827* (2013.01); *G01N 33/70* (2013.01); *G01N 33/74* (2013.01); *G01N 33/84* (2013.01); *G01N 33/948* (2013.01)

(58) Field of Classification Search
USPC .............................................. 436/94; 422/420
See application file for complete search history.

(56) References Cited

U.S. PATENT DOCUMENTS

| | | | |
|---|---|---|---|
| 4,775,058 A | 10/1988 | Yatsko | |
| 4,934,817 A | 6/1990 | Gassenhuber | |
| 5,518,689 A | 5/1996 | Dosmann et al. | |
| 5,654,803 A | 8/1997 | Howard, III et al. | |
| 5,877,863 A | 3/1999 | Ross et al. | |
| 6,528,323 B1 | 3/2003 | Thayer et al. | |
| 6,767,710 B2 | 7/2004 | DiNello et al. | |
| 7,313,257 B2 | 12/2007 | Roman | |
| 10,161,928 B2 | 12/2018 | Dahl et al. | |
| 2005/0202399 A1 | 9/2005 | Yonehara et al. | |
| 2009/0155921 A1 | 6/2009 | Lu et al. | |
| 2011/0223673 A1 | 9/2011 | Profitt | |
| 2011/0275162 A1 | 11/2011 | Xie et al. | |
| 2012/0184462 A1 | 7/2012 | O'Farrell et al. | |
| 2013/0267032 A1 | 10/2013 | Tsai et al. | |
| 2014/0028857 A1 | 1/2014 | Jasperse | |
| 2014/0349326 A1 | 11/2014 | Ingber | |
| 2015/0301031 A1 | 10/2015 | Zin et al. | |
| 2016/0195553 A1 | 7/2016 | Wang et al. | |
| 2016/0222432 A1 | 8/2016 | Lee | |
| 2018/0059027 A1 | 3/2018 | Chen et al. | |
| 2018/0059129 A1 | 3/2018 | Dewar | |
| 2020/0386753 A1 | 12/2020 | Somes et al. | |

FOREIGN PATENT DOCUMENTS

| | | |
|---|---|---|
| WO | 2005001444 A1 | 1/2005 |
| WO | 2009063185 A1 | 5/2009 |
| WO | 2010120917 A2 | 10/2010 |
| WO | 2010120917 A3 | 1/2011 |

OTHER PUBLICATIONS

Suzanne Hodsden, Stanford's New Take On The At-Home Urinalysis Test, News Feature, Med Device Online, published May 23, 2016, available at: http://www.meddeviceonline.com/doc/stanford-s-new-take-on-the-at-home-urinalysis-test-0001 (last accessed: Feb. 8, 2022).

Written Opinion of the ISA for International Patent App. No. PCT/CA2020/050985, mailed Nov. 9, 2020, 8 pages.

URINALYSIS TEST STRIP FOR OVER-THE-COUNTER USE

CROSS-REFERENCE TO RELATED APPLICATIONS

This application is a § 371 National Stage Entry of International Patent Application No. PCT/CA2020/050985, filed Jul. 15, 2020, claiming the benefit of priority of Canadian Patent Application No. 3,049,972, filed Jul. 15, 2019, the entireties of which are incorporated by reference into this application.

FIELD

The present technology is directed to urinalysis test strips that detect analyte levels associated with the urine of healthy individuals. More specifically the technology is colorimetric urinalysis test strips that are highly sensitive to analyte levels found in normal urine and provide continuous data within a concentration range.

BACKGROUND

Colorimetric assays have been used for determining metabolite levels. For example, European Patent Application No. 437254A2 discloses the enzymatic determination of creatinine in aqueous solutions, the creatinine contained in the sample is converted by means of creatinine iminohydrolase into 1-methylhydantoin and a first molecule of $NH_3$, the 1-methylhydantoin formed is converted by means of ATP-dependent 1-methylhydantoinase and N-carbamoylsarcosine amidohydrolase into sarcosine, $CO_2$ and a second molecule of $NH_3$, and the two molecules of $NH_3$ formed are determined together. A test strip was not used and the metabolite level was determined spectrophotometrically.

US Publication No. 20050202399 discloses a highly reliable method of measuring an analyte in a sample using a redox reaction. In this method, a formazan compound is added to a sample prior to a redox reaction so as to eliminate the influence of any reducing substance in the sample. Thereafter, a reducing substance or an oxidizing substance derived from the analyte is formed, and the amount of the formed substance is measured by the redox reaction. The amount of the analyte is determined from the amount of the formed substance thus measured. As the formazan compound, for example, 1-(4-iodophenyl)-3-(2,4-disulfophenyl)-5-(2,4-dinitrophenyl) formazan can be used. A test strip was not used and the analyte level was determined spectrophotometrically.

Most colorimetric continuous data urinalysis test strips have reagent pads with sensitivity levels and ranges designed for symptomatic (non-healthy) people. This is because urinalysis is traditionally an initial step in the medical diagnosis of various disease or sickness. To assist with such diagnosis, the sensitivity levels (detection thresholds) and ranges of the reagent pads are designed for people with excessive levels of glucose, total protein, albumin, ketone, creatinine, sodium, bilirubin, urobilinogen, nitrites, leukocytes, and other analytes in their urine. In other cases of diagnosis, the sensitivity levels and ranges of reagent pads are designed for people with deficient levels of sodium, creatinine, or other analytes in their urine. These excessive or deficient analyte levels are a result of impaired liver, impaired kidney or other impaired organ functions associated with various disease states. In addition, there are other types of urinalysis test strips known as lateral flow immunoassays (also known as immunochromatographic assays, or also known as binary immunoassays), which measure the presence or absence of an analyte at a selected concentration level of the analyte. Examples of such binary immunoassay test strips include test strips designed to measure estrogen at various levels, luteinizing hormone (LH) at various levels, or THC—COOH (full chemical name of 11-Nor-9-carboxy-Δ9-tetrahydrocannabinol, and also known as 11-COOH—THC, or known as 11-nor-9-carboxy-THC, or known as THC-11-oic acid) at various levels.

For example, US Publication No. 20160222432 discloses a test strip using formaldehyde or peroxide, which are sarcosine metabolites, for diagnosing prostate cancer, and a method for diagnosing prostate cancer by means of the test strip. No range of the metabolites was disclosed.

U.S. Pat. No. 10,161,928 discloses a panel for monitoring levels of biomarkers, including an assay having at least one inflammation monitoring test, at least one oxidative stress monitoring test, and at least one antioxidant activity monitoring test. A method of monitoring an individual's health, by collecting a sample from the individual, applying the sample to an assay panel, performing at least one inflammation monitoring test, at least one oxidative stress monitoring test, and at least one antioxidant activity monitoring test in the panel, and determining levels of biomarkers related to inflammation, oxidative stress, and antioxidant activity and therefore providing information regarding the individual's relative health and/or risk of developing one or more diseases. The test strips are limited to detection of markers associate with poor health or stress.

With regard to prior art for colorimetric continuous data test strips for specific analytes, glucose tests have a minimum detectable level of 25 mg/dL to 100 mg/dL depending on the manufacturer, as they are intended for the diagnosis of glycosuria. Such diagnosis may occur when levels of glucose in urine are at least 200 mg/dL, but likely 500 mg/dL or higher. For example, the Siemens' Multistix® test strip has a several reagent pads, one of which is for measurement of glucose in urine. The glucose reagent pad can resolve several resolution levels for glucose in urine corresponding to 100 mg/dL (green), 250 mg/dL, 500 mg/dL, 1000 mg/dL or 2000+ mg/dL (brown). For healthy adults the normal range of glucose in urine may be from 0.1-15 mg/dL with an average of 6 mg/dL. For normal healthy adults on a fasting diet the range of glucose in urine may be 2-20 mg/dL. Therefore, the Multistix® test strip, or test strips with similar measurement levels by other manufacturers, cannot be used for measuring the variation of glucose in urine of normal healthy people. This is because they are not sufficiently sensitive to levels of glucose in urine of normal healthy people, and also do not have sufficient colorimetric resolution to resolve between different concentrations at these normal levels.

With regard to fructose and sucrose, the measurement of each of sucrose and fructose levels in urine has been found to be a good indicator of dietary sugar consumption by healthy people. Such measurement would have great benefit for people to measure the amount of sugar they have consumed via various foods and diets. Furthermore, levels of sucrose and fructose consumption have been correlated to obesity, which has implications for a person's health. The level of fructose is correlated to the amount of fruit-derived sugar, while the level of sucrose is correlated to the amount of refined sugar (white sugar). Several analytical methods are available for the quantitative determination of sucrose and fructose at the low concentrations associated with the normal urine of healthy persons. These include spectrophotometric analysis of enzyme assays and Gas Chromatography/Mass Spectrometry. Such methods and equipment can provide accurate quantitative continuous data measures of low levels of sugar in urine, however they are not suitable for home use or point-of-care use.

With regard to protein, the measurement of total protein levels and albumin levels in the urine of healthy people has been found to be an indicator of exercise intensity. In particular, it was found that moderate to high intensity exercise or sport correlates to the levels of total protein, albumin, nitrite, leukocyte, pH, and specific gravity of urine of healthy people and athletes. Measurement of urinary total protein and albumin can have great benefit for people and athletes who are on various exercise and fitness programs involving high intensity activity. Measurement of urinary total protein and albumin in urine can help inform the person to adjust their high intensity activity to achieve specific outcomes. In particular, from a sport physiological point of view, the urinary proteome could provide indications as to the nutritional and training status of an athlete. That way, muscle damage may be identified by myoglobin and its fragments in urine or erythrocytosis by the detection of hemoglobin or other erythrocyte-derived proteins. These parameters may be used for training control and modulation.

Traditional colorimetric continuous data test strips for measuring total protein or albumin are intended for assisting in detection of proteinuria in symptomatic people, and hence have minimum detectable levels for total protein of 30 mg/dL, or minimum detectable levels for albumin of 10-30 mg/dL, depending on the manufacturer. For example, the Siemens' Multistix® test strip has a several reagent pads, one of which is for measurement of total protein in urine. The total protein reagent pad can resolve several resolution levels for total protein in urine corresponding to 30 mg/dL, 100 mg/dL, 300 mg/dL, and 2000+ mg/dL. Therefore, the Multistix® test strip, or test strips with similar purpose and measurement levels by other manufacturers, are not suitable for measuring the low-level variation of total protein in urine of normal healthy people. This is because they are not sufficiently sensitive to normal levels of total protein in urine, and also do not have sufficient colorimetric resolution to resolve between different concentrations at these normal levels.

Several analytical methods are available for the quantitative determination of protein at the low concentrations associated with the normal urine of healthy persons. These include spectrophotometric analysis of enzyme assays and Gas Chromatography/Mass Spectrometry. Such methods and equipment can provide accurate quantitative continuous data measures of low levels of protein in urine, however they are not suitable for home use or point-of-care use.

For healthy adults the normal range of sodium in urine is 20 mmol/L to 40 mmol/L (46 mg/dL to 84 mg/dL). A urine sodium level less than 20 mmol/L may be indicative of hypovolemia. A urine sodium level of 40 mmol/L or more is associated with a number of disease states. Prior art test strips intended for the purpose of diagnosis of symptomatic people actually measure chloride levels in urine, with the assumption that sodium levels correlate to chloride levels. Such chloride-based test strips are not cleared by the Food and Drug Administration for measurement of sodium in urine.

Some analytes can be detected using chemical reactions or using immunoassays. Of existing urinalysis immunoassay test strips, the vast majority of those are lateral flow immunoassay test strips, (also known as immunochromatographic assays, or also known as binary immunoassays) which are test strips that indicate one of a positive result, a negative result, or an inconclusive result. Lateral flow immunoassay test strips are designed with a pre-defined specific "threshold" analyte concentration before they indicate a positive result. Given this positive/negative result associated with a single concentration level, such test strips are not suitable for measuring variations in analyte levels over time or in relation to a specific condition, for example, during weight loss or throughout an athletic training program.

With regard to estrogen a woman's level may be in the range of 60-400 picograms per millilitre (pg/mL). To detect estrogen in urine, a lateral flow immunoassay strip may be designed with a detection threshold concentration of 200 pg/mL. If the estrogen concentration present in a sample of urine is below 200 pg/mL the test strip will indicate a negative result (appearance of a red stripe) at one location of the strip. If the concentration is above 200 pg/mL the test strip will indicate a positive result with a red stripe appearing at another location of the strip. If there is a problem with the test for a number of possible reasons, the test strip may indicate an inconclusive result with a red stripe appearing at a third location of the strip. Thus, such a test will only inform the user if they are above or below the predesigned threshold concentration of the test strip. Hence, the binary test strips cannot show a continuous color variation over a range of concentrations. Continuous colorimetric color variation would allow a woman to gain a better understanding of the variation of estrogen concentration levels and can correlate those various levels to health. Similarly, detection of testosterone is binary, with the results either being positive, which is indicative of levels above a predetermined level, or negative, which is indicative of levels below a predetermined level.

Luteinizing hormone (LH) in women, has a close relation to fertility since it affects the ovaries, and in men it also has a relation to fertility since it triggers testosterone production, and hence effects sperm production. For ovulation in women, it is reported that an LH threshold of 25-30 mIU/mL is indicative of probable ovulation in the next 24 hours. LH also plays a role in puberty and menstruation. For conventional lateral flow immunoassay test strips for LH measurement, there are several different available test strips. Each different test strip has an LH detection threshold, such as either 20, 25, 30, 35, or 40 mIU/mL. These are individual binary test strips, each made to indicate a result above or below one threshold. Hence, the binary test strips cannot show a continuous color variation over a range of LH concentrations, which would allow a woman to more accurately determine the time of ovulation, or to measure LH variations over time in relation to health.

THC—COOH is a metabolite formed in the body after cannabis (tetrahydrocannabinol, or THC) is consumed, where THC—COOH is present in the urine. THC—COOH has a full chemical name of 11-Nor-9-carboxy-Δ9-tetrahydrocannabinol (also known as 11-COOH—THC or, 11-nor-9-carboxy-THC, or THC-11-oic acid). THC—COOH concentration in the blood and hence concentration in the urine will spike to a high level after a person consumes cannabis. The THC—COOH concentration in urine will gradually decrease in an exponential manner for a period up to 30 days or longer, depending on initial volume of cannabis consumption and body metabolism. Therefore, measurement of the concentration of THC—COOH in a person's urine can be correlated to the recent history of cannabis consumption by person. Furthermore, for certain industrial jobs, or for permission to operate machinery or equipment, or for insurance purposes, there are restrictions on the allowable level of THC—COOH in a person's urine, since it is known that there is a correlation between recent cannabis consumption and the resulting levels of THC—COOH in urine. Further, during rehabilitation, it is important to accurately track THC—COOH in a patient. Present testing methods are done with binary immunoassays and therefore only detect the presence or absence of TCH—COOH at a specific selected concentration. Hence, the binary test strips cannot show a continuous color variation over a range of concentrations, which restricts the utility of the testing methods.

SUMMARY

A non-binary test strip that allows a user to measure the level of specific analytes in the urine of a normal, healthy individual is provided. The test strip provides a color response to a minor change in analyte levels, in other words, continuous data is produced. The test strip can be read by comparing the results to a color legend or can be read using an electronic reader designed for in-home OTC use or using an electronic reader designed for point-of-care use, as disclosed in U.S. patent application Ser. No. 16/166,052. The analytes include glucose, fructose, sucrose, total protein, albumin, sodium, potassium, calcium, and estrogen, luteinizing hormone (LH) and THC—COOH. In addition, the traditional analytes such as nitrites, leukocytes, ketone, creatinine, chloride, ascorbic acid, as well as the physical properties of pH and specific gravity are combined on the test strips.

In one embodiment, a test strip for urinalysis is provided, the test strip including a reagent pad for detecting a concentration of a selected analyte, the reagent pad attached to the test strip and comprising a substrate and an analyte detection system retained thereon, the analyte detection system including a plurality of components necessary for detection of the selected analyte with a resolution of at least three analyte concentrations.

The test strip may include at least two reagent pads for detecting a concentration of a selected analyte, each reagent pad attached to the test strip and comprising the substrate and an analyte detection system retained thereon.

In the test strip, each reagent pad may be for a different selected analyte and each reagent pad includes the plurality of components necessary for detection of that analyte.

In the test strip, the different selected analytes may be sucrose and glucose.

In the test strip, the analyte detection system for sucrose may detect sucrose and glucose and the analyte detection system for glucose may detect glucose.

In the test strip, the analyte detection system for sucrose may include beta-fructosidase, glucose oxidase, peroxidase and either chromogenic substrate or fluorogenic substrate and the analyte detection system for glucose may include glucokinase (GK), phosphoglucose isomerase (PGI), nicotinamide adenine dinucleotide phosphate (NADP+) or nicotinamide adenine dinucleotide (NAD+), glucose-6-phosphate dehydrogenase (G6PdH), ATP and magnesium.

The test strip may further comprise a reagent pad with an analyte detection system for fructose.

In the test strip, the analyte detection system for fructose may include fructokinase (FK), phosphoglucose isomerase (PGI), nicotinamide adenine dinucleotide phosphate (NADP+) or nicotinamide adenine dinucleotide (NAD+), glucose-6-phosphate dehydrogenase (G6PdH), adenosine triphosphate (ATP) and magnesium.

In the test strip, one of the plurality of component of at least one reagent pad may be a protein.

In the test strip, the protein may be an enzyme.

In the test strip, the enzyme may be a hexokinase.

In the test strip, the protein may be an antibody or an antibody fragment which is conjugated with a conjugate to provide a conjugated antibody or a conjugated antibody fragment.

In the test strip, the conjugated antibody or the conjugated antibody fragment may be one of a conjugated anti-hormone antibody, a conjugated anti-THC—COOH antibody, a conjugated anti-albumin antibody and a plurality of total protein conjugated antibodies.

In the test strip, the conjugate may be a fluorescent moiety.

In the test strip, the reagent pads may have an accuracy of less than about ±10%.

In the test strip, the reagent pads may have an accuracy of less than about ±5%.

In another embodiment, a reagent pad for use in urinalysis to detect a continuous concentration range of a selected analyte is provided, the reagent pad comprising a substrate and an analyte detection system retained thereon, the analyte detection system including a plurality of components necessary for detection of the selected analyte.

The reagent pad may have an accuracy of less than about ±10%.

In the reagent pad, the accuracy may be less than about ±5%.

In the reagent pad, one of the plurality of components may be a protein.

In the reagent pad, the protein may be an enzyme.

In the reagent pad, the enzyme may be a hexokinase.

In the reagent pad, the protein may be an antibody or an antibody fragment which is conjugated with a conjugate to provide a conjugated antibody or a conjugated antibody fragment.

In the reagent pad, the conjugated antibody or the conjugated antibody fragment may be one of a conjugated anti-hormone antibody, a conjugated anti-THC—COOH antibody, a conjugated anti-albumin antibody and a plurality of total protein conjugated antibodies.

In the reagent pad, the conjugate may be a fluorescent moiety.

In the reagent pad, the reagent pad may have a detection range of about 0.1 mg/dL to about 20 mg/dL of sucrose.

In the reagent pad, the reagent pad may have a detection range of about 0.1 mg/dL to about 20 mg/dL of fructose.

In the reagent pad, the reagent pad may have a detection range of about 0.1 mg/dL to about 15 mg/dL of glucose.

In the reagent pad, the reagent pad may have a detection range of about 1 mg/dL to about 25 mg/dL of total protein.

In the reagent pad, the reagent pad may have a detection range of about 0.1 mg/dL to about 6 mg/dL of albumin.

In the reagent pad, the reagent pad may have a detection range of about 20 mg/dL to about 60 mg/dL of calcium.

In the reagent pad, the reagent pad may have a detection range of about 110 to about 250 mmol/L of chloride.

In another embodiment, a method of manufacturing a urinalysis reagent pad is provided, the method comprising: selecting an analyte detection system and a pad; loading a plurality of components of the analyte detection system onto the pad, with the exception of a variable component; immobilizing the variable component at a range of amounts on the pad, thereby manufacturing a urinalysis reagent pad.

In the reagent pad, the range of amounts of the variable component may be a continuous range.

In the reagent pad, the immobilizing may be printing.

In the reagent pad, the printing may be nanoprinting.

In another embodiment, a method of detecting sodium and potassium in urine is provided, the method comprising: selecting a lateral flow system or a reagent pad which includes β-galactosidase, 5-bromo-4-chloro-3-indolyl-β-d-galactopyranoside and magnesium; wetting the lateral flow system or the reagent pad with urine; and measuring a color change.

In another embodiment, a method of detecting calcium in urine is provided, the method comprising selecting a lateral flow system or a reagent pad which is configured to detect a range of about 20 mg/dL to about 60 mg/dL calcium, with at least three or more levels of resolution in the range; wetting the lateral flow system or the reagent pad with urine; and measuring a color change.

In the method, the lateral flow system or the reagent pad may include ammonium purpurate.

In another embodiment, a reagent pad for use in urinalysis to detect a continuous concentration range of a selected analyte, the reagent pad comprising a substrate and an analyte detection system retained thereon, the analyte detection system including a plurality of components necessary for detection of the selected analyte, wherein at least one of the plurality of components is a variable component, the variable component immobilized on the substrate at a continuous plurality of different amounts on the reagent pad.

In the reagent pad, the variable component may be printed on the substrate.

In the reagent pad, the variable component may be nanoprinted on the substrate.

In the reagent pad, the continuous plurality of different amounts may provide discrimination of at least three concentrations of the analyte.

In the reagent pad, the variable component may provide an accuracy less than about ±10%.

In the reagent pad, the variable component may be a protein.

In the reagent pad, the protein may be an enzyme.

In the reagent pad, the enzyme may be a hexokinase.

In the reagent pad, the protein may be an antibody or an antibody fragment, which is conjugated with a conjugate to provide a conjugated antibody or a conjugated antibody fragment.

In the reagent pad, the conjugated antibody or the conjugated antibody fragment may be one of a conjugated anti-hormone antibody, a conjugated anti-THC—COOH antibody, a conjugated anti-albumin antibody and a plurality of total protein conjugated antibodies.

In the reagent pad, the conjugate may be a fluorescent moiety.

The reagent pad may have a detection range of about 0.1 mg/dL to about 20 mg/dL of sucrose.

The reagent pad may have a detection range of about 0.1 mg/dL to about 20 mg/dL of fructose.

The reagent pad may have a detection range of about 0.1 mg/dL to about 15 mg/dL of glucose.

The reagent pad may have a detection range of about 1 mg/dL to about 25 mg/dL of total protein.

The reagent pad may have a detection range of about 0.1 mg/dL to about 6 mg/dL of albumin.

The reagent pad may have a detection range of about 20 mg/dL to about 60 mg/dL of calcium.

The reagent pad may have a detection range of about 110 to about 250 mmol/L of chloride.

In another embodiment, a lateral flow system for use in urinalysis to detect a continuous concentration range of a selected analyte is provided, the lateral flow system comprising a substrate and an analyte detection system retained thereon, the analyte detection system including a plurality of components necessary for detection of the selected analyte, wherein at least one of the plurality of components is a variable component, the variable component immobilized on the substrate at a continuous plurality of different amounts on the lateral flow system.

In the lateral flow system, the variable component may be printed on the substrate.

In the lateral flow system, the variable component may be nanoprinted on the substrate.

In the lateral flow system, the continuous plurality of different amounts may provide discrimination of at least three concentrations of the analyte.

In the lateral flow system, the variable component may provide an accuracy of less than about ±10%.

In the lateral flow system, the variable component may be a protein.

In the lateral flow system, the protein may be an enzyme.

In the lateral flow system, the enzyme may be a hexokinase.

In the lateral flow system, the protein may be an antibody or an antibody fragment, which is conjugated with a conjugate to provide a conjugated antibody or a conjugated antibody fragment.

In the lateral flow system, the conjugated antibody or the conjugated antibody fragment may be one of a conjugated anti-hormone antibody, a conjugated anti-THC—COOH antibody, a conjugated anti-albumin antibody and a plurality of total protein conjugated antibodies.

In the lateral flow system, the conjugate may be a fluorescent moiety.

The lateral flow system may have a detection range of about 0.1 mg/dL to about 20 mg/dL of sucrose.

The lateral flow system may have a detection range of about 0.1 mg/dL to about 20 mg/dL of fructose.

The lateral flow system may have a detection range of about 0.1 mg/dL to about 15 mg/dL of glucose.

The lateral flow system may have a detection range of about 1 mg/dL to about 25 mg/dL of total protein.

The lateral flow system may have a detection range of about 0.1 mg/dL to about 6 mg/dL of albumin.

The lateral flow system may have a detection range of about 20 mg/dL to about 60 mg/dL of calcium.

The lateral flow system may have a detection range of about 110 to about 250 mmol/L of chloride.

The lateral flow system may have a detection range of about 20 mmol/L to about 40 mmol/L of sodium.

The lateral flow system may have a detection range of about 25 mE/L to about 125 mE/L potassium.

The reagent pad may have a detection range of about 25 to about 125 mE/L of potassium.

The reagent pad may have a detection range of about 20 mmol/L to 40 mmol/L of sodium.

DESCRIPTION

Except as otherwise expressly provided, the following rules of interpretation apply to this specification: (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, the terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Definitions

Quantitative data—in the context of the present technology, quantitative data is comprised of continuous data and discrete data.

Continuous data—in the context of the present technology, continuous data is a quantitative data set consisting of rational numbers.

Rational number—in the context of the present technology, a rational number is a real number that may be a whole number or a fraction or a decimal.

Test strip—in the context of the present technology, a test strip also called a reagent strip or a dipstick, is a narrow strip of plastic with one or more reagent pads attached to it. Each reagent pad is comprised of a substrate material that contains all the necessary chemical reagents that react with a desired analyte in urine. Test strips are stored dry, together with a desiccant in the sealed container. When a urinalysis test is done, upon dipping the test strip with reagent pad(s) in urine, the reagent materials become chemically active for the necessary reaction chemistry.

Lateral flow immunoassay—in the context of the present technology, lateral flow immunoassay (or immunochromatographic assay) test strips are test strips with a single long substrate pad, which has several different areas of different function. Generally, one end of the substrate pad is temporarily dipped in the urine, and then the urine laterally flows from one end of the pad to the other end over a few minutes, by capillary action of the porous substrate. As the urine flows, it sequentially passes through various areas (zones) on the pad that contain various chemical reagents (antibodies, chromogens, and others) that sequentially interact with the desired analytes in urine to produce a response. The response will be a positive result or a negative result (binary), or they indicate a spoiled test. The response is visible as a colored stripe (usually red), and the color is either clearly visible or not visible (binary). Binary immunoassay test strips are designed to detect a specific sensitivity level (threshold level) of an analyte concentration in urine before they indicate a positive result.

Colorimetric test strips—in the context of the present technology, colorimetric test strips are test strips whereby the substrate pad contains all of the necessary chemical reagents that react with the desired analyte in urine. All of the chemical reagents are located together on the same area throughout the pad. When the pad is immersed in urine and removed, the chemical reaction takes place over 0-3 minutes depending on the chemistry, to produce a color which is proportional to the concentration of the analyte in the urine.

Resolution—in the context of the present technology, resolution refers to levels of results, such as color change that can be unambiguously and reliably differentiated from one another.

Accuracy—in the context of the present technology, accuracy is statistically determined as a measure of variability about a mean, for example standard deviation or standard error.

Range—in the context of the present technology, range is the difference between a minimum sensitivity level below which there is no detectable result and a maximum sensitivity above which there is no further detectable change in the result.

Fine resolution—in the context of the present technology, fine resolution refers to discrimination between analyte concentrations varying by ±10%, preferably ±5% and more preferably ±2.5%.

Analyte detection system—in the context of the present technology, the analyte detection system is all the components necessary for the analyte to be detected. It is retained on the reagent pad.

Variable component—in the context of the present technology, the variable component is the component in the analyte detection system that controls the amount of analyte detected. It is immobilized on the reagent pad and varies in concentration across the pad and between pads.

Antibody—in the context of the present technology, an antibody is one or more of a monoclonal antibody, a polyclonal antibody or an antibody fragment.

DETAILED DESCRIPTION

When a healthy person is living normally, or is undergoing a diet program (such as the Ketone diet, the Atkin's diet, the Vegan diet, or other diets), or is undergoing an exercise, fitness or body-building program, the levels of various analytes in urine such as glucose, sucrose, fructose, total protein, albumin, ketone, creatinine, sodium, potassium, calcium, chloride, and ascorbic acid, as well as the physical properties of pH and specific gravity will vary naturally, and provide important information to the person. The measured real number values of these analyte concentrations can help inform the person to, for example, but not limited to adjust their daily living routine, adjust their diet, or adjust their exercise program, to achieve specific outcomes.

Figure 1:
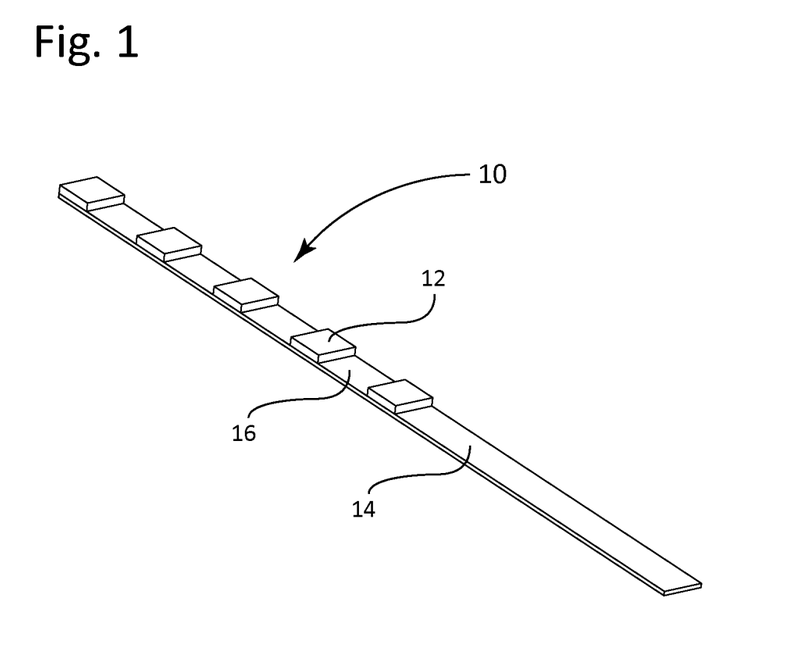
FIG. 1 is a schematic of a urinalysis test strip of the present technology.

In one embodiment, a test strip, generally referred to as 10 is shown in FIG. 1. It has about 7 reagent pads 12, each for measurement of a different analyte or for measurement of a different concentration of one or more analytes. The reagent pads 12 are retained on a water-resistant substrate 14 and separated from one another by a space 16. The reagent pads 12 are highly sensitive to the level of analyte and provide a continuous color response to a selected range of concentrations of analytes. Each reagent pad has an accuracy of about ±10%, preferably about ±10%. Each reagent pad has a resolution of at least three analyte concentrations.

Figure 2A:
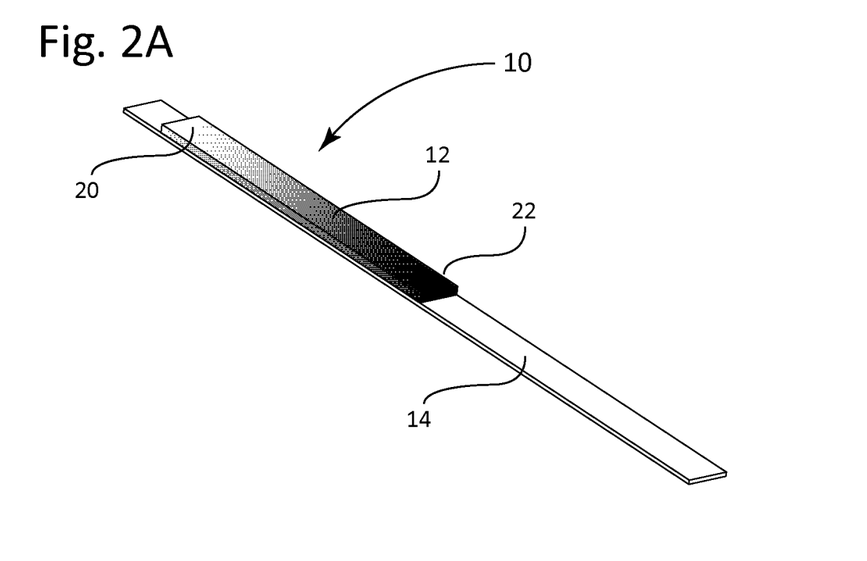
FIG. 2A is a schematic of an alternative embodiment of the reagent test strip of FIG. 1

A schematic of an alternative embodiment of a test trip 10 with one reagent pad 12 is shown in FIG. 2A. It can be seen that the amount of the variable component increases across the surface of the reagent pad 12, as indicated by the increase in shading. At a first side 20, the variable component is at the lowest amount for detection of the analyte or is at the lower limit of the selected concentration of the analyte and at the second side 22, the variable component is at the amount of analyte selected to be the highest to be reported. The variable component is preferably printed with a nanoprinter to obtain the desired resolution and range and is immobilized. The remaining components of the analyte detection system are provided at concentrations necessary to saturate the reactions at the highest concentration of analyte to be detected.

High Resolution, Continuous Response Reagent Pads for Healthy Individuals

Fructose

In one embodiment, one reagent pad 12 is a colorimetric reagent pad for measuring fructose in urine. It has a range of about 0.1 to about 20 mg/dL and has at least three or more levels of resolution. It is an enzyme-based reagent pad.

The reagent pad includes fructokinase (FK), phosphoglucose isomerase (PGI), nicotinamide adenine dinucleotide phosphate (NADP+) or nicotinamide adenine dinucleotide (NAD+), glucose-6-phosphate dehydrogenase (G6PdH), adenosine triphosphate (ATP), magnesium, at least one binder, at least one stabilizer and any cofactors and coenzymes needed for the reactions.

FK is a hexokinase enzyme that facilitates phosphorylation of fructose to fructose-6-phosphate (F6P). Then, the F6P reacts with phosphoglucose isomerase (PGI) to produce G6P. The resulting G6P produced from that reaction, together with nicotinamide adenine dinucleotide phosphate (NADP+) or nicotinamide adenine dinucleotide (NAD+), is catalyzed by glucose-6-phosphate dehydrogenase (G6PdH) to produce gluconate-6-phosphate, as well as NADPH or NADH and a hydrogen (H+).

NADPH and NADH both absorb ultraviolet (UV) light with UV absorption at 340 nm+/−30 nm. NADPH and NADH have a fluorescent emission peak at 460 nm+/−50 nm, which is visible light in the blue-green range (NAD and NADP do not have this peak). The intensity of the fluorescent emission is proportional to the amount of NADPH (or NADH) present, which is in turn proportional to the amount of glucose, which is in turn proportional to the amount of fructose present in the urine sample.

In an alternative embodiment, the reagent pad includes glucokinase (GK), phosphoglucose isomerase (PGI), nicotinamide adenine dinucleotide phosphate (NADP+) or nicotinamide adenine dinucleotide (NAD+), glucose-6-phosphate dehydrogenase (G6PdH), ATP, magnesium, at least one binder and at least one stabilizer. GK is a hexokinase enzyme that facilitates phosphorylation of both glucose and fructose.

To manufacture the colorimetric fructose reagent pad, the concentration and volume of each of FK or GK, PGI, G6PdH, NADP+ or NAD+, ATP and magnesium applied to the substrate are specifically selected to maximize the fluorescent color response (intensity) of the reagent pad to fructose in urine, for the desired sensitivity levels, desired range, and desired resolution for fructose in the urine of healthy people. For example, a single reagent pad can be used to discriminate between about 0.1 mg/dL, about 5 mg/dL, about 10 mg/dL, about 15 mg/dL and about 20 mg/dL. Also, additional chemical reagents or chemical processes may be used to stabilize reagent materials and to keep them in dry form on the dry reagent pad during storage, so that when a urinalysis test is done upon dipping the reagent pad in urine, the reagent materials become active for the necessary reaction chemistry.

Note, if the urine sample contains both fructose and glucose and GK is used rather than FK, the described fructose reagent pad will detect the total concentration of both fructose and glucose.

In another embodiment, one reagent pad 12 is a colorimetric reagent pad for measuring fructose in urine. It has a range of about 0.1 to about 20 mg/dL and has at least three or more levels of resolution. It is a chemical-based reagent pad. A single reagent pad can be used to discriminate between about 0.1 mg/dL, about 5 mg/dL, about 10 mg/dL, about 15 mg/dL and about 20 mg/dL.

Reaction detection can be done with colorimetry, reflection spectroscopy, or fluorescence, depending on the chemistry.

Glucose

In one embodiment, one reagent pad 12 is a colorimetric reagent pad for measuring glucose in urine. It has a range of about 0.1 to about 15 mg/dL and has at least three or more levels of resolution. It is an enzyme-based reagent pad.

The reagent pad includes glucokinase (GK), phosphoglucose isomerase (PGI), nicotinamide adenine dinucleotide phosphate (NADP+) or nicotinamide adenine dinucleotide (NAD+), glucose-6-phosphate dehydrogenase (G6PdH), ATP, magnesium, at least one binder, at least one stabilizer and any cofactors and coenzymes necessary for the reactions.

To manufacture the colorimetric glucose reagent pad, the concentration and volume of each of GK, PGI, G6PdH, NADP+ or NAD+, ATP and magnesium applied to the substrate are specifically selected to maximize the fluorescent color response (intensity) of the reagent pad to glucose in urine, for the desired sensitivity levels, desired range, and desired resolution for glucose in the urine of healthy people. For example, a single reagent pad can be used to discriminate between about 0.1 mg/dL, about 5 mg/dL, about 7.5 mg/dL, about 10 mg/dL, about 12.5 mg/dL and about 15 mg/dL. Also, additional chemical reagents or chemical processes may be used to stabilize reagent materials and to keep them in dry form on the dry reagent pad during storage, so that when a urinalysis test is done upon dipping the reagent pad in urine, the reagent materials become active for the necessary reaction chemistry.

In another embodiment, one reagent pad 12 is a colorimetric reagent pad for measuring glucose in urine. It has a range of about 0.1 to about 15 mg/dL and has at least three or more levels of resolution. It is a chemical-based reagent pad. A single reagent pad can be used to discriminate between about 0.1 mg/dL, about 5 mg/dL, about 7.5 mg/dL, about 10 mg/dL, about 12.5 mg/dL and about 15 mg/dL.

Reaction detection can be done with colorimetry, reflection spectroscopy, or fluorescence, depending on the chemistry.

Sucrose

In one embodiment, one reagent pad 12 is a colorimetric reagent pad for measuring sucrose in urine. It has a range of about 0.1 to about 20 mg/dL and has at least three or more levels of resolution. It is an enzyme-based reagent pad.

The reagent pad includes Beta-fructosidase, glucokinase (GK), phosphoglucose isomerase (PGI), nicotinamide adenine dinucleotide phosphate (NADP+) or nicotinamide adenine dinucleotide (NAD+), glucose-6-phosphate dehydrogenase (G6PdH), ATP, magnesium, at least one binder, at least one stabilizer and any cofactors and coenzymes necessary for the reactions.

Beta-fructosidase is an enzyme that together with water (or urine), acts upon sucrose to produce fructose and glucose in a stoichiometric ratio. The glucose and fructose are then catalyzed by glucokinase to produce fructose-6-phosphate (F6P) and glucose-6-phosphate (G6P). The F6P reacts with phosphoglucose isomerase (PGI) to produce G6P. The resulting G6P produced from that reaction, together with nicotinamide adenine dinucleotide phosphate (NADP+) or nicotinamide adenine dinucleotide (NAD+), is catalyzed by glucose-6-phosphate dehydrogenase (G6PdH) to produce gluconate-6-phosphate, as well as NADPH or NADH and a hydrogen (H+).

NADPH and NADH both absorb ultraviolet (UV) light with UV absorption at 340 nm+/−30 nm. NADPH and NADH have a fluorescent emission peak at 460 nm+/−50 nm, which is visible light in the blue-green range (NAD+ and NADP+ do not have this peak). The intensity of the fluorescent emission is proportional to the amount of NADPH (or NADH) present, which is in turn proportional to the amount of glucose, which is in turn proportional to the amount of sucrose present in the urine sample.

To manufacture the colorimetric sucrose reagent pad, the concentration and volume of each of Beta-fructosidase, GK, PGI, G6PdH, NADP+ or NAD+, ATP, and magnesium applied to the substrate are specifically selected to maximize the fluorescent color response (intensity) of the reagent pad to sucrose in urine, for the desired sensitivity levels, desired range, and desired resolution for sucrose in the urine of healthy people. For example, a single reagent pad can be used to discriminate between about 0.1 mg/dL, about 5 mg/dL, about 10 mg/dL, about 15 mg/dL and about 20 mg/dL. Also, additional chemical reagents or chemical processes may be used to stabilize reagent materials and to keep them in dry form on the dry reagent pad during storage, so that when a urinalysis test is done upon dipping the reagent pad in urine, the reagent materials become active for the necessary reaction chemistry. Note, if the urine sample contains a mixture of sucrose, and one or more of glucose and fructose, the described sucrose reagent pad will detect the total concentration of these sugars.

In another embodiment, one reagent pad 12 is a colorimetric reagent pad for measuring sucrose in urine. It has a range of about 0.1 to about 20 mg/dL and has at least three or more levels of resolution. It is a chemical-based reagent pad. A single reagent pad can be used to discriminate between about 0.1 mg/dL, about 5 mg/dL, about 10 mg/dL, about 15 mg/dL and about 20 mg/dL.

Reaction detection can be done with colorimetry, reflection spectroscopy, or fluorescence, depending on the chemistry.

In another embodiment, one reagent pad 12 is a colorimetric reagent pad for measuring sucrose in urine. It has a range of about 0.1 to about 20 mg/dL and has at least three or more levels of resolution. It is a combination approach of both an enzyme-based and chemical-based reagent pad. A single reagent pad can be used to discriminate between about 0.1 mg/dL, about 5 mg/dL, about 10 mg/dL, about 15 mg/dL and about 20 mg/dL. In one embodiment, Beta-fructosidase catalyzes the breakdown of sucrose to produce fructose and glucose in a stoichiometric ratio. The glucose is then oxidized to gluconic acid and hydrogen peroxide by glucose oxidase. Hydrogen peroxide reacts with o-dianisidine in the presence of peroxidase to form a colored product.

In another embodiment, Beta-fructosidase catalyzes the breakdown of sucrose to produce fructose and glucose in a stoichiometric ratio. The glucose is then oxidized to gluconic acid and hydrogen peroxide by glucose oxidase. Hydrogen peroxide reacts with potassium iodide in the presence of peroxidase to form a colored product.

In another embodiment, Beta-fructosidase catalyzes the breakdown of sucrose to produce fructose and glucose in a stoichiometric ratio. The glucose is then oxidized to gluconic acid and hydrogen peroxide by glucose oxidase. Hydrogen peroxide reacts with OxiRed Probe (e.g., a peroxidase fluorogenic substrate like those sold by Abcam®) in a 1:1 stoichiometry to produce the red fluorescent oxidation product, resorufin. The resorufin is quantified by colorimetric ($\lambda$max=570 nm) or fluorometric methods (Ex/Em=535/587 nm).

To manufacture the colorimetric sucrose reagent pad, the concentration and volume of each of Beta-fructosidase, glucose oxidase, peroxidase and chromogenic substrate or fluorogenic substrate applied to the substrate are specifically selected to maximize the fluorescence or color response (intensity) of the reagent pad to sucrose in urine, for the desired sensitivity levels, desired range, and desired resolution for sucrose in the urine of healthy people. For example, a single reagent pad can be used to discriminate between about 0.1 mg/dL, about 5 mg/dL, about 10 mg/dL, about 15 mg/dL and about 20 mg/dL. Also, additional chemical reagents or chemical processes may be used to stabilize reagent materials and to keep them in dry form on the dry reagent pad during storage, so that when a urinalysis test is done upon dipping the reagent pad in urine, the reagent materials become active for the necessary reaction chemistry. Note, if the urine sample contains a mixture of sucrose and glucose, the described sucrose reagent pad will detect the total concentration of these sugars.

In a preferred embodiment, there is a test strip that allows for the specific detection of each of sucrose, glucose and fructose. A first reagent pad measures sucrose and glucose. Beta-fructosidase, glucose oxidase, peroxidase and chromogenic substrate or fluorogenic substrate are applied to the substrate of the reagent pad in addition to at least one binder and at least one stabilizer and any cofactors or coenzymes needed for the reactions. A second reagent pad measures glucose. The reagent pad includes glucokinase (GK), phosphoglucose isomerase (PGI), nicotinamide adenine dinucleotide phosphate (NADP+) or nicotinamide adenine dinucleotide (NAD+), glucose-6-phosphate dehydrogenase (G6PdH), ATP, magnesium, at least one binder, at least one stabilizer and any cofactors and coenzymes necessary for the reactions. A third reagent pad measures fructose. The reagent pad includes fructokinase (FK), phosphoglucose isomerase (PGI), nicotinamide adenine dinucleotide phosphate (NADP+) or nicotinamide adenine dinucleotide (NAD+), glucose-6-phosphate dehydrogenase (G6PdH), adenosine triphosphate (ATP), magnesium, at least one binder, at least one stabilizer and any cofactors and coenzymes needed for the reactions. The amount of glucose measured from the second pad is subtracted from the total amount of sucrose and glucose from the first reagent pad in order to determine the amount of sucrose.

Reaction detection can be done with colorimetry, reflection spectroscopy, or fluorescence, depending on the chemistry.

In one embodiment, the test strip 10 comprises a reagent pad 12 for glucose, a reagent pad 12 for fructose and a reagent pad 12 for sucrose. These may be enzymatic or chemical based.

Total Protein

In one embodiment, one reagent pad 12 is a colorimetric reagent pad for measuring total protein in urine. It has a range of about 0.1 to about 25 mg/dL and has at least three or more levels of resolution.

The reagent pad is based on the bicinchoninic acid assay and includes bicinchoninic acid, sodium carbonate, sodium bicarbonate, sodium tartrate, and copper(II) sulfate pentahydrate, a strong base to provide a pH of about 11.25 at least one binder and at least one stabilizer.

To manufacture the colorimetric total protein reagent pad, the concentration and volume of each of bicinchoninic acid, sodium carbonate, sodium bicarbonate, sodium tartrate, and copper(II) sulfate pentahydrate and the strong base applied to the substrate are specifically selected to maximize the color response (intensity) of the reagent pad to total protein in urine, for the desired sensitivity levels, desired range, and desired resolution for protein in the urine of healthy people. For example, a single reagent pad can be used to discriminate between about 0.1 mg/dL, about 5 mg/dL, about 10 mg/dL, about 15 mg/dL, about 20 mg/dL and about 25 mg/dL. Also, additional chemical reagents or chemical processes may be used to stabilize reagent materials and to keep them in dry form on the dry reagent pad during storage.

In another embodiment, a colorimetric total protein reagent pad for use on test strips, to measure total protein in urine associated with healthy people, is provided. The following considerations were taken into account: (i) The concentration and volume of the chromogen used, and/or the type of chromogen used can be changed, and/or (ii) The concentration and volume of the acid buffer used, and/or the type of acid buffer used can be changed, and/or (iii) The type of substrate material comprising the reagent pad can be changed. These approaches are specifically done to maximize the color response of the reagent pad to total protein in urine, for the desired sensitivity levels, desired range, and desired resolution for total protein in the urine of healthy people.

In another embodiment, one reagent pad 12 is a colorimetric reagent pad for measuring total protein in urine. It has a range of about 0.1 to about 25 mg/dL and has at least three or more levels of resolution. It is an antibody-based reagent pad.

Urine from 20 participants was pooled and total proteins were purified from the pool. Antibodies were raised against the mixture of proteins found in urine to provide a battery of antibodies. The battery of antibodies was conjugated with a Dylight Fluor (e.g., a fluorescent conjugate), preferably Dylight Fluor 488. To manufacture the colorimetric total protein reagent pad, the antibodies were immobilized on the reagent pad, which included a suitable buffer. The concentration and volume applied to the substrate were specifically selected to maximize the color response (intensity) of the reagent pad to total protein in urine, for the desired sensitivity levels, desired range, and desired resolution for total protein in the urine of healthy people. For example, a single reagent pad can be used to discriminate between about 0.1 mg/dL, about 5 mg/dL, about 10 mg/dL, about 15 mg/dL, about 20 mg/dL and about 25 mg/dL. Also, additional chemical reagents or chemical processes may be used to stabilize reagent materials and to keep them in dry form on the dry reagent pad during storage.

Reaction detection can be done with colorimetry, reflection spectroscopy, or fluorescence, depending on the conjugate that is bound to the antibody.

Albumin

In another embodiment, one reagent pad 12 is a colorimetric reagent pad for measuring albumin in urine. It has a range of about 0.1 to about 6 mg/dL and has at least three or more levels of resolution. It is an antibody-based reagent pad.

The anti-albumin antibodies were conjugated with a Dylight Fluor, preferably Dylight Fluor 488. To manufacture the colorimetric albumin reagent pad, the antibodies were immobilized on the reagent pad, which included a suitable buffer. The concentration and volume applied to the substrate were specifically selected to maximize the color response (intensity) of the reagent pad to albumin in urine, for the desired sensitivity levels, desired range, and desired resolution for albumin in the urine of healthy people. For example, a single reagent pad can be used to discriminate between about 0.1 mg/dL, about 2 mg/dL, about 4 mg/dL, about 5 mg/dL and about 6 mg/dL. Also, additional chemical reagents or chemical processes may be used to stabilize reagent materials and to keep them in dry form on the dry reagent pad during storage.

Reaction detection can be done with colorimetry, reflection spectroscopy, or fluorescence, depending on the conjugate that is bound to the antibody.

High Resolution, Continuous Response Reagent Pads or Lateral Flow Systems

Sodium

In another embodiment, one reagent pad 12 is a colorimetric reagent pad for measuring sodium in urine. It has a range of about 46 to about 82 mg/dL and has at least three or more levels of resolution for healthy individuals, or a range of 0.1 to about 46 mg/dL for unhealthy individuals deficient in sodium, or a range of 82 to about 122 mg/dL for unhealthy individuals with excessive sodium.

The reagent pad 12 includes β-galactosidase, 5-bromo-4-chloro-3-indolyl-β-d-galactopyranoside, (X-gal), magnesium, at least one binder, at least one stabilizer and any cofactors and coenzymes necessary for the reactions.

To manufacture the colorimetric sodium reagent pad, the concentration and volume of β-galactosidase, X-gal, and magnesium applied to the substrate are specifically selected to maximize the color response (intensity) of the reagent pad to sodium in urine, for the desired sensitivity levels, desired range, and desired resolution for sodium in the urine of healthy people and unhealthy individuals. For example, a single reagent pad can be used to discriminate between about 46 mg/dL, about 54 mg/dL, about 62 mg/dL, about 72 mg/dL and about 82 mg/dL for healthy individuals. For example, a single reagent pad can be used to discriminate between about 0.1 mg/dL, about 10 mg/dL, about 20 mg/dL, about 30 mg/dL and about 46 mg/dL for unhealthy individuals. For example, another single reagent pad can be used to discriminate between about 82 mg/dL, about 92 mg/dL, about 102 mg/dL, about 112 mg/dL and about 122 mg/dL. Also, additional chemical reagents or chemical processes may be used to stabilize reagent materials and to keep them in dry form on the dry reagent pad during storage.

Reaction detection can be done with colorimetry, reflection spectroscopy, or the principle of fluorescence.

In an alternative embodiment, a lateral flow system may be utilized instead of the reagent pad.

Chloride

In another embodiment, one reagent pad 12 is a colorimetric reagent pad for measuring chloride in urine. It has a range of about 110 to about 250 milli equivalents/Liter (mE/L) for healthy individuals and has at least three or more levels of resolution. The reagent pad 12 includes diethyl-p-phenylene diamine, at least one binder and at least one stabilizer.

To manufacture the colorimetric chlorine reagent pad, the concentration and volume of diethyl-p-phenylene diamine applied to the substrate is specifically selected to maximize the color response (intensity) of the reagent pad to chlorine in urine, for the desired sensitivity levels, desired range, and desired resolution for chlorine in the urine of healthy people and unhealthy individuals. For example, a single reagent pad can be used to discriminate between about 110 mE/L, about 150 mE/L, about 175 mg/dL, about 200 mg/dL and about 250 mE/L for a healthy individual. For example, a single reagent pad can be used to discriminate between about 0.1 mE/L, about 25 mE/L, about 50 mE/L, about 75 mE/L, about 100 mE/L and about 110 mE/L for an unhealthy individual. For example, another single reagent pad can be used to discriminate between about 250 mE/L, about 275 mE/L, about 300 mE/L, about 325 mE/L and about 350 mE/L in an unhealthy individual. Also, additional chemical reagents or chemical processes may be used to stabilize reagent materials and to keep them in dry form on the dry reagent pad during storage.

In an alternative embodiment, a lateral flow system may be utilized instead of the reagent pad.

Potassium

In another embodiment, one reagent pad 12 is a colorimetric reagent pad for measuring potassium in urine. It has a range of about 25 to about 125 mE/L and has at least three or more levels of resolution.

The reagent pad 12 includes β-galactosidase, 5-bromo-4-chloro-3-indolyl-β-d-galactopyranoside, (X-gal), magnesium, at least one binder, at least one stabilizer and any cofactors and coenzymes necessary for the reactions.

To manufacture the colorimetric potassium reagent pad, the concentration and volume of β-galactosidase, X-gal, and magnesium applied to the substrate are specifically selected to maximize the color response (intensity) of the reagent pad to potassium in urine, for the desired sensitivity levels, desired range, and desired resolution for potassium in the urine of healthy people. For example, a single reagent pad can be used to discriminate between about 25 mE/L, about 50 mE/L, about 75 mE/L, about 100 mE/L and about 125 mE/L in a healthy individual. For example, a single reagent pad can be used to discriminate between about 0.1 mE/L, about 5 mE/L, about 10 mE/L, about 15 mE/L, about 20 mE/L and about 25 mE/L for an unhealthy individual. For example, another single reagent pad can be used to discriminate between about 125 mE/L, about 150 mE/L, about 175 mE/L, about 200 mE/L and about 225 mE/L in an unhealthy individual. Also, additional chemical reagents or chemical processes may be used to stabilize reagent materials and to keep them in dry form on the dry reagent pad during storage.

Note that this reaction also detects sodium, hence a second embodiment utilizes the chloride test to estimate the amount of sodium in the urine.

In an alternative embodiment, a lateral flow system may be utilized instead of the reagent pad.

Calcium

In another embodiment, one reagent pad 12 is a colorimetric reagent pad for measuring calcium in urine. It has a range of about 20 mg/dL to about 60 mg/dL and has at least three or more levels of resolution.

The reagent pad 12 includes ammonium purpurate, at least one binder, at least one stabilizer and any cofactors and coenzymes necessary for the reactions.

To manufacture the colorimetric the concentration and volume of ammonium purpurate applied to the substrate are specifically selected to maximize the color response (intensity) of the reagent pad to calcium in urine, for the desired sensitivity levels, desired range, and desired resolution for calcium in the urine of healthy people. For example, a single reagent pad can be used to discriminate between about 20 mg/dL, to about 30 mg/dL, to about 40 mg/dL, to about 50 mg/dL and to about 60 mg/dL in a healthy individual. For example, a single reagent pad can be used to discriminate between about 0.1 mg/dL, about 5 mg/dL, about 10 mg/dL, about 15 mg/dL and about 20 mg/dL for an unhealthy individual. For example, another single reagent pad can be used to discriminate between about 60 mg/dL, about 80 mg/dL, about 100 mg/dL, about 120 mg/dL and about 140 mg/dL in an unhealthy individual. Also, additional chemical reagents or chemical processes may be used to stabilize reagent materials and to keep them in dry form on the dry reagent pad during storage.

In an alternative embodiment, a lateral flow system may be utilized instead of the reagent pad.

High Resolution, Continuous Response Urinalysis Test Strips for Healthy Individuals In another embodiment, a test strip includes the reagent pads as described above for each of glucose, sucrose, fructose, total protein, albumin, calcium, sodium, chloride and potassium.

In another embodiment, a test strip includes at least three reagent pads as described above, and reagent pads for pH, specific gravity, ketones, creatinine and ascorbic acid.

In another embodiment, a colorimetric test strip includes at least two of the reagent pads as described above for the detection of glucose, sucrose, fructose, sodium, total protein, albumin and reagent pads for each of nitrites, leukocytes, pH, specific gravity, ketones, creatinine and ascorbic acid.

High Resolution, Continuous Response Urinalysis Test Strips

In one embodiment, test strips include a number of reagent pads of different sensitivity and range for a given analyte. The reagent pads each have a high resolution and there is high resolution between the reagent pads. The response within a reagent pad is continuous and the response between the reagent pads is also continuous. In this manner, a highly accurate measure of an individual's level of a specific analyte is obtained.

For example, if the test strip is for glucose measurement, such a test strip may have three reagent pads A, B and C whereby pad A is sensitive to glucose concentrations in urine in the range of about 0.1 to about 5 mg/dL, pad B is sensitive to concentrations in the range of about 5 mg/dL to about 10 mg/dL and reagent pad C is sensitive to concentrations in the range of about 10 mg/dL to about 15 mg/dL. As another example, a test strip for glucose measurement may have only two pads A and B, whereby pad A is sensitive to glucose concentrations in the range of about 0.1 mg/dL to about 10 mg/dL, pad B is sensitive to concentrations in the range of about 10 to about 50 mg/dL. There is a continuous response both within and between reagent pads. As another example, a test strip for glucose measurement may have four reagent pads A, B, C, and D, or may have more reagent pads, where each pad is sensitive to various analyte concentration ranges. As another example, a test strip may have at least two pads or more pads, where the sensitivity levels or ranges overlap, which helps by providing redundant measurement to ensure accuracy. For example, a test strip for glucose measurement may have three reagent pads A, B and C whereby pad A is sensitive to glucose concentrations in urine in the range of 0.1-10 mg/dL, pad B is sensitive to concentrations in the range of 5-20 mg/dL and Pad C is sensitive to concentrations in the range of 15-50 mg/dL.

In another embodiment, the urinalysis test strip has multiple reagent pads for measuring an analyte in the urine, whereby each reagent pad has a different reagent chemistry and hence has a different sensitivity level and range for that analyte in urine. The reagent pads were selected to provide a continuous response over an analyte concentration range for healthy individuals or unhealthy individuals or both. The analytes measured include glucose, sucrose, fructose, total protein, albumin, ketone, creatinine, sodium, potassium, calcium, chloride, estrogen, luteinizing hormone (LH) and THC—COOH. The test strips have at least two or more reagent pads for a given analyte, with each reagent pad having a different sensitivity level and range for the analyte. For three or more reagent pads, the response within and between pads is continuous with high resolution within and between pads. In one embodiment the ranges overlap and in another embodiment they do not overlap. In this embodiment, there may be two or more reagent pads of differing sensitivities for one analyte and two or more reagent pads of differing sensitivities for a second analyte or a second and third analyte or second, third and fourth analyte. Alternatively, there may be two or more reagent pads of differing sensitivities and ranges for a given analyte with the remainder of the reagent pads selected for different analytes. The test strip may also include reagent pads for pH, specific gravity, bilirubin, urobilinogen, nitrites, and leukocytes.

Reagent Pad and Test Strip for Hormones

In another embodiment, one reagent pad 12 is a colorimetric reagent pad for measuring LH in urine. It has a range of about 10 to about 60 milli International Units (mIU)/mL or about 20 to about 40 mIU/mL and has at least three or more levels of resolution. It is an antibody-based reagent pad.

The anti-LH antibodies were conjugated with colloidal gold or Alexa Fluor (e.g., a fluorescent dye), preferably Alexa Fluor 750. To manufacture the colorimetric LH reagent pad, the antibodies were immobilized on the reagent pad, which included a suitable buffer. The concentration and volume applied to the substrate were specifically selected to maximize the color response (intensity) of the reagent pad to LH in urine, for the desired sensitivity levels, desired range, and desired resolution for LH in the urine of healthy people. For example, a single reagent pad can be used to discriminate between about 10 mIU/mL, about 20 mIU/mL, about 30 mIU/mL, about 40 mIU/mL, about 50 mIU/mL, and about 60 mIU/mL. Also, additional chemical reagents or chemical processes may be used to stabilize reagent materials and to keep them in dry form on the dry reagent pad during storage. Reaction detection can be done with colorimetry, reflection spectroscopy, or fluorescence, depending on the conjugate that is bound to the antibody.

In one embodiment, test strips include a number of reagent pads of different sensitivity and range for LH. The reagent pads each have a high resolution and there is high resolution between the reagent pads. The response within a reagent pad is continuous and the response between the reagent pads is also continuous. In this manner, a highly accurate measure of an individual's level of LH is obtained.

In another embodiment, one reagent pad 12 is a colorimetric reagent pad for measuring estrogen in urine. It has a range of about 60 picograms (pg)/mL to about 400 pg/mL and has at least three or more levels of resolution. It is an antibody-based reagent pad.

The anti-estrogen antibodies were conjugated with colloidal gold or Alexa Fluor, preferably Alexa Fluor 750; To manufacture the colorimetric estrogen reagent pad, the antibodies were immobilized on the reagent pad, which included a suitable buffer. The concentration and volume applied to the substrate were specifically selected to maximize the color response (intensity) of the reagent pad to estrogen in urine, for the desired sensitivity levels, desired range, and desired resolution for LH in the urine of healthy people. For example, a single reagent pad can be used to discriminate between about 60 pg/mL to about 100 pg/mL, to about 150 pg/mL, to about 200 pg/mL, to about 250 pg/mL, to about 300 pg/mL, to about 350 pg/mL and to about 400 pg/mL. Also, additional chemical reagents or chemical processes may be used to stabilize reagent materials and to keep them in dry form on the dry reagent pad during storage. Reaction detection can be done with colorimetry, reflection spectroscopy, or fluorescence, depending on the conjugate that is bound to the antibody.

In one embodiment, test strips include a number of reagent pads of different sensitivity and range for estrogen. The reagent pads each have a high resolution and there is high resolution between the reagent pads. The response within a reagent pad is continuous and the response between the reagent pads is also continuous. In this manner, a highly accurate measure of an individual's level of estrogen is obtained.

A method of monitoring estrogen levels in individuals undergoing hormone replacement therapy, being treated for low estrogen levels or in transgender females, during and after transitioning involves using the reagent pad or the test strip.

In another embodiment, one reagent pad 12 is a colorimetric reagent pad for measuring testosterone in urine. It has a range of about 60 picograms (pg)/mL to about 400 pg/mL and has at least three or more levels of resolution. It is an antibody-based reagent pad.

The anti-testosterone antibodies were conjugated with colloidal gold or Alexa Fluor, preferably Alexa Fluor 750. To manufacture the colorimetric estrogen reagent pad, the antibodies were immobilized on the reagent pad, which included a suitable buffer. The concentration and volume applied to the substrate were specifically selected to maximize the color response (intensity) of the reagent pad to testosterone in urine, for the desired sensitivity levels, desired range, and desired resolution for LH in the urine of healthy people. For example, a single reagent pad can be used to discriminate between about 60 pg/mL to about 100 pg/mL, to about 150 pg/mL, to about 200 pg/mL, to about 250 pg/mL, to about 300 pg/mL, to about 350 pg/mL and to about 400 pg/mL. Also, additional chemical reagents or chemical processes may be used to stabilize reagent materials and to keep them in dry form on the dry reagent pad during storage. Reaction detection can be done with colorimetry, reflection spectroscopy, or fluorescence, depending on the conjugate that is bound to the antibody.

In one embodiment, test strips include a number of reagent pads of different sensitivity and range for testosterone. The reagent pads each have a high resolution and there is high resolution between the reagent pads. The response within a reagent pad is continuous and the response between the reagent pads is also continuous. In this manner, a highly accurate measure of an individual's level of testosterone is obtained.

A method of monitoring testosterone levels in individuals being treated for high or low levels of testosterone or in transgender females, during and after transitioning involves using the reagent pad or the test strip.

In another embodiment, the test strips include at least one reagent pad for estrogen and at least one reagent pad for testosterone. The reagent pads each have a high resolution and there is high resolution between the reagent pads. The response within a reagent pad is continuous and the response between the reagent pads is also continuous. In this manner, highly accurate measures of an individual's levels of estrogen and testosterone are obtained.

A method of monitoring testosterone and estrogen levels in individuals being treated for abnormal hormone levels or in transgender females, during and after transitioning involves using the reagent pad or the test strip.

Reagent Pad and Test Strip for TCH—COOH

In another embodiment, one reagent pad 12 is a colorimetric reagent pad for measuring THC—COOH in urine. It has a range of about 1 ng/mL to about 150 ng/mL and has at least three or more levels of resolution. It is an antibody-based reagent pad or antibody fragment-based reagent pad.

The anti-THC—COOH antibodies were conjugated with colloidal gold or Alexa Fluor, preferably Alexa Fluor 750. To manufacture the colorimetric estrogen reagent pad, the antibodies were immobilized on the reagent pad, which included a suitable buffer. The concentration and volume applied to the substrate were specifically selected to maximize the color response (intensity) of the reagent pad to THC—COOH in urine, for the desired sensitivity levels, desired range, and desired resolution for THC—COOH in the urine of users of marijuana and marijuana products. For example, a single reagent pad can be used to discriminate between about 1 ng/mL, to about 20 ng/mL, to about 40 ng/mL, to about 60 ng/mL, to about 80 ng/mL, to about 100 ng/mL, to about 120 ng/mL, to about 130 ng/mL, and to about 150 ng/mL. Also, additional chemical reagents or chemical processes may be used to stabilize reagent materials and to keep them in dry form on the dry reagent pad during storage. Reaction detection can be done with colorimetry, reflection spectroscopy, or fluorescence, depending on the conjugate that is bound to the antibody.

In one embodiment, test strips include a number of reagent pads of different sensitivity and range for THC—COOH. The reagent pads each have a high resolution and there is high resolution between the reagent pads. The response within a reagent pad is continuous and the response between the reagent pads is also continuous. In this manner, a highly accurate measure of an individual's level of testosterone is obtained.

A method of monitoring THC—COOH in patients undergoing rehabilitation involves using the reagent pad or the test strip for detection of TCH—COOH. The sensitivity and resolution allows for accurate tracking of the patient's usage.

Method of Manufacture of Reagent Pad of First Embodiment

The reagent pads have a substrate which was selected to retain the components of the analyte detection system.

Suitable substrates include carboxymethyl-cellulose, starch, collagen, modified Sepharose (e.g., a crosslinked, beaded-form of agarose, a polysaccharide polymer material extracted from seaweed; hereinafter "Sepharose"), ion exchange resins, active charcoal, silica, aluminum oxide, titanium, diatomaceous earth, hydroxyapatite, ceramic, agarose or treated porous glass which is an organic material and certain polymers. One of the desired properties of support matrix is the mesoporous material where the large surface areas and greater number of pores will lead to higher analyte detection system loading per unit mass. Porous supports are generally preferred as the high surface area permits a higher analyte detection system loading. The pore parameters and particle size of the support establish the total surface area and thus affect the capacity for retaining of the analyte detection system.

Method of Manufacture of Reagent Pad of Second Embodiment

The reagent pads have a substrate which was selected to retain the components of the analyte detection system.

Suitable substrates include carboxymethyl-cellulose, starch, collagen, modified Sepharose, ion exchange resins, active charcoal, silica, aluminum oxide, titanium, diatomaceous earth, hydroxyapatite, ceramic, agarose or treated porous glass which is an organic material and certain polymers. One of the desired properties of support matrix is the mesoporous material where the large surface areas and greater number of pores will lead to higher analyte detection system loading per unit mass. Porous supports are generally preferred as the high surface area permits a higher analyte detection system loading. The pore parameters and particle size of the support establish the total surface area and thus affect the capacity for retaining of the analyte detection system.

A variable component is in each analyte detection system. The variable component was immobilized on the substrate and controls the amount of analyte that is detected. The variable component is selected on the basis of ease of immobilized and reaction kinetics. For example, but not limited to the variable component in the enzymatic reactions was one or more enzymes; the variable component in the chemical reactions was the reactant; and the variable component in the immunological reactions was the antibody. The variable component was immobilized by physical adsorption, entrapment or covalent attachment or cross linking.

The variable component was immobilized in a separate step to the loading of the reagent pad with the remainder of the analyte detection system components. The lowest concentration of the variable component needed to produce a detectable signal in terms of fluorescence or color was determined for each analyte. This concentration or the desired concentration for a lower limit of analyte needing to be detected, was immobilized on one side of the reagent pad, with the concentration of the variable component increasing across the reagent pad. This was accomplished by printing the reagent pad at very high resolution. Similarly, if multiple reagent pads were used on a test strip, the concentration increased from reagent pad to reagent pad. Again, the reagent pads were printed at high resolution, preferably with a nanoprinter.

Example 1

Figure 2B:
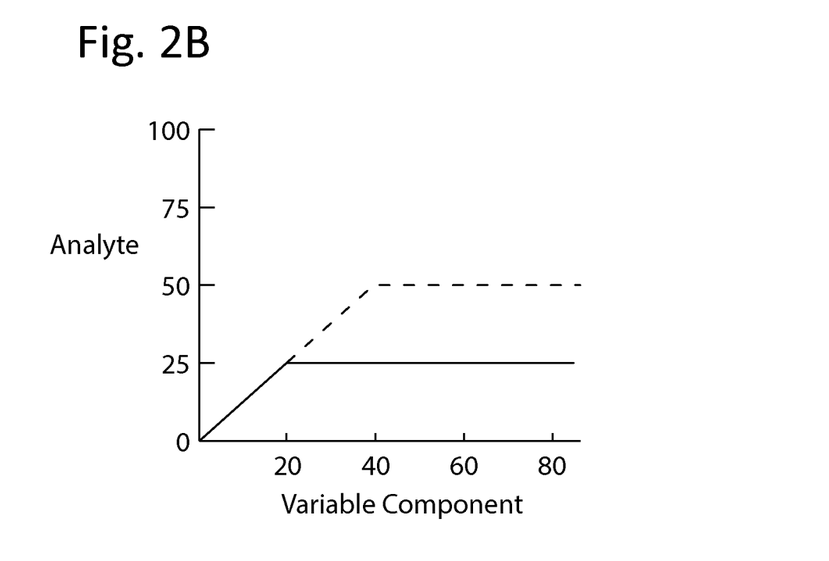
FIG. 2B is an exemplary graph showing results from the reagent test strip of FIG. 2A.

As shown in FIG. 2A, in an exemplary example the variable component detects from 1 nmol/L to 100 nmol/L of the selected analyte, with the concentration of the variable component increasing from left to right. As shown in FIG. 2B, the urine sample contains 25 nmol/L of the selected analyte, hence the intensity of the response (colorimetric or fluorescence, for example) increases with increasing concentration of the variable component until the amount of the selected analyte becomes limiting. The graph then levels off (at 25 nmol/L). The inflection point on the graph is equivalent to the concentration of analyte in the sample. If the urine sample contains 50 nmol/L of the selected analyte, the intensity of the response (colorimetric or fluorescence, for example) increases with increasing concentration of the variable component until the amount of the selected analyte becomes limiting (at 50 nmol/L). The graph then levels off. The inflection point on the graph is equivalent to the concentration of analyte in the sample. This allows for very accurate pin-pointing of the concentration of analyte, and provides continuous data.

Method of Manufacture of Lateral Flow System

The lateral flow systems have a substrate which was selected to retain the components of the analyte detection system.

Suitable substrates include carboxymethyl-cellulose, starch, collagen, modified Sepharose, ion exchange resins, active charcoal, silica, aluminum oxide, titanium, diatomaceous earth, hydroxyapatite, ceramic, agarose or treated porous glass which is an organic material and certain polymers. One of the desired properties of support matrix is the mesoporous material where the large surface areas and greater number of pores will lead to higher analyte detection system loading per unit mass. Porous supports are generally preferred as the high surface area permits a higher analyte detection system loading. The pore parameters and particle size of the support establish the total surface area and thus affect the capacity for retaining of the analyte detection system.

A variable component is in each analyte detection system. The variable component was immobilized on the substrate and controls the amount of analyte that is detected. The variable component is selected on the basis of ease of immobilized and reaction kinetics. For example, but not limited to the variable component in the enzymatic reactions was one or more enzymes; the variable component in the chemical reactions was the reactant; and the variable component in the immunological reactions was the antibody. The variable component was immobilized by physical adsorption, entrapment or covalent attachment or cross linking.

The variable component was immobilized in a separate step to the loading of the lateral flow system with the remainder of the analyte detection system components. The lowest concentration of the variable component needed to produce a detectable signal in terms of fluorescence or color was determined for each analyte. This concentration or the desired concentration for a lower limit of analyte needing to be detected, was immobilized on one side of the reagent pad, with the concentration of the variable component increasing across the reagent pad. This was accomplished by printing the reagent pad at very high resolution. Similarly, if multiple reagent pads were used on a test strip, the concentration increased from reagent pad to reagent pad. Again, the reagent pads were printed at high resolution, preferably with a nanoprinter.

Example 2

Figure 3A:
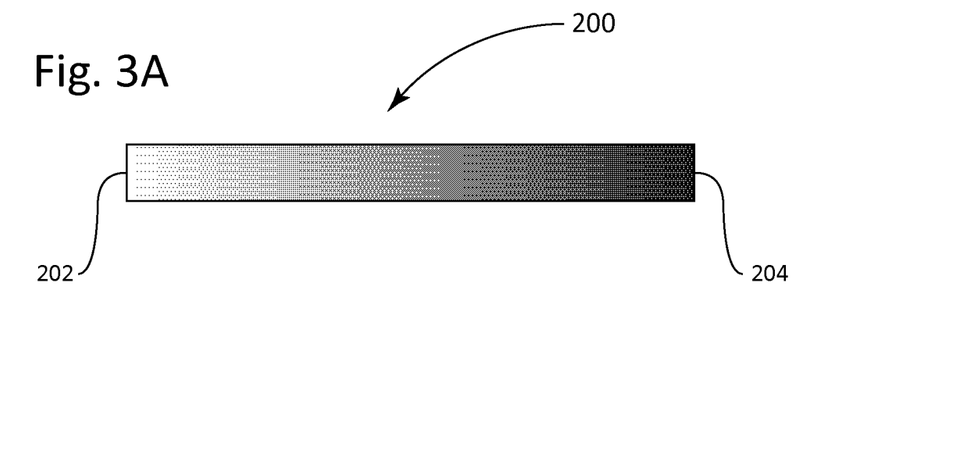
FIG. 3A is a schematic of a lateral flow strip of the present technology and FIG. 3B is an exemplary graph showing results from the lateral flow strips.
Figure 3B:
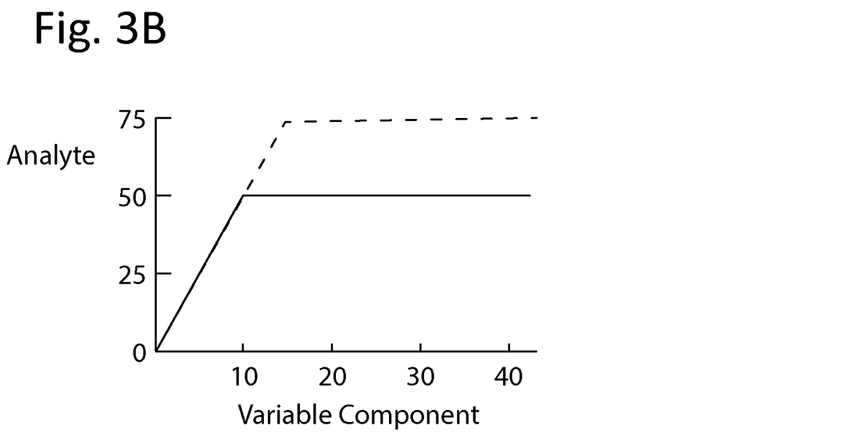

As shown in FIG. 3A, the lateral flow system, generally referred to as 200, has an increasing amount of the variable component from a first side 202 to a second side 204. In an exemplary example the variable component detects from 1 nmol/L to 100 nmol/L of the selected analyte. As shown in FIG. 3B, the urine sample contains 50 nmol/L of the selected analyte, hence the intensity of the response (colorimetric or fluorescence, for example) increases with increasing concentration of the variable component until the amount of the selected analyte becomes limiting. The graph then levels off. The inflection point on the graph is equivalent to the concentration of analyte in the sample. If the urine sample contains 75 nmol/L of the selected analyte, the intensity of the response (colorimetric or fluorescence, for example) increases with increasing concentration of the variable component until the amount of the selected analyte becomes limiting (at 75 nmol/L). The graph then levels off. The inflection point on the graph is equivalent to the concentration of analyte in the sample. This allows for very accurate pin-pointing of the concentration of analyte, and provides continuous data.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize or be able to ascertain using no more than routine experimentation, many equivalents to the specific example embodiments specifically described herein. For example, the stated analyte concentrations detected in the cited ranges are exemplary and the actual concentrations may differ, for example, but not limited to the stated concentrations of 20 mg/dL, to about 30 mg/dL, to about 40 mg/dL, to about 50 mg/dL and to about 60 mg/dL between 20 mg/dL and 60 mg/dL may actually be 35 mg/dL, to about 45 mg/dL, to about 55 mg/dL, to about 60 mg/dL. Such equivalents are intended to be encompassed in the scope of the claims, if appended hereto or subsequently filed.

The invention claimed is:

1. A test strip for urinalysis, the test strip comprising:
at least two reagent pads for detecting concentrations of different analytes in urine;
each reagent pad of the at least two reagent pads being attached to the test strip and comprising a substrate and an analyte detection system;
each analyte detection system comprising a plurality of components operable to detect a selected analyte of the different analytes in the urine;
wherein the different analytes comprise sucrose and glucose;
wherein the at least two reagent pads comprise a colorimetric reagent pad, an analyte detection system for sucrose that detects the sucrose in the urine, and an analyte detection system for glucose that detects the glucose in the urine; and wherein the analyte detection system for sucrose comprises a first plurality of components comprising beta-fructosidase, glucose oxidase, and peroxidase.

2. The test strip of claim 1, wherein one or both of
the analyte detection system for sucrose has a detection range of about 0.1 mg/dl to about 20 mg/dL of the sucrose in the urine; and
the analyte detection system for glucose has a detection range of about 0.1 mg/dl to about 15 mg/dl of the glucose in the urine.

3. The test strip of claim 1, wherein the plurality of components for each analyte detection system is operable to detect the selected analyte with a resolution of at least three concentrations.

4. The test strip of claim 1, comprising a chromogenic substrate or a fluorogenic substrate applied to the substrate of any reagent pad of the at least two reagent pads.

5. The test strip of claim 1, wherein the at least two reagent pads comprise:
a first reagent pad comprising the analyte detection system for sucrose; and
a second reagent pad comprising the analyte detection system for glucose.

6. The test strip of claim 1, wherein the analyte detection system for glucose comprises a second plurality of components comprising glucokinase (GK), phosphoglucose isomerase (PGI), nicotinamide adenine dinucleotide phosphate (NADP+) or nicotinamide adenine dinucleotide (NAD+), glucose-6-phosphate dehydrogenase (G6PdH), ATP, and magnesium.

7. The test strip of claim 1, wherein the different analytes comprise fructose.

8. The test strip of claim 7, wherein the at least two reagent pads further comprise an analyte detection system for fructose that detects the fructose in the urine.

9. The test strip of claim 8, wherein the at least two reagent pads further comprise a separate reagent pad comprising the analyte detection system for fructose.

10. The test strip of claim 8, wherein the analyte detection system for fructose has a detection range of about 0.1 mg/dl to about 20 mg/dl of the fructose in the urine.

11. The test strip of claim 8, wherein the analyte detection system for fructose comprises a third plurality of components comprising fructokinase (FK), phosphoglucose isomerase (PGI), nicotinamide adenine dinucleotide phosphate (NADP+), nicotinamide adenine dinucleotide (NAD+), glucose-6-phosphate dehydrogenase (G6PdH), adenosine triphosphate (ATP), and magnesium.

12. The test strip of claim 1, wherein the plurality of components of the analyte detection system of any reagent pad of the at least two reagent pads comprise one of:
a protein;
an enzyme;
a hexokinase;
an antibody;
an antibody fragment;
a conjugated antibody;
a conjugated antibody fragment;
a conjugated anti-hormone antibody;
a conjugated anti-THC—COOH antibody;
a conjugated anti-albumin antibody;
a plurality of total protein conjugated antibodies;
ammonium purpurate; or
b-galactosidase, 5-bromo-4-chloro-3-indolyl-P-d-galactopyranoside, and magnesium.

13. The test strip of claim 12, wherein one of the conjugated antibody, the conjugated antibody fragment, the conjugated anti-hormone antibody, the conjugated anti-THC—COOH antibody, the conjugated anti-albumin antibody, and the plurality of total protein conjugated antibodies was conjugated with a conjugate comprising a fluorescent moiety.

14. The test strip of claim 1, wherein each reagent pad of the at least two reagent pads provides an accuracy of less than about 10%.

15. The test strip of claim 1, wherein the plurality of components of one reagent pad of the at least two reagent pads comprise a detection range of:
about 0.1 mg/dL to about 20 mg/dl of the sucrose in the urine;
about 0.1 mg/dl to about 15 mg/dL of the glucose in the urine;
about 0.1 mg/dL to about 20 mg/dL of fructose in the urine;
about 1 mg/dl to about 25 mg/dL of total protein in the urine;
about 0.1 mg/dl to about 6 mg/dL of albumin in the urine;
about 20 mg/dL to about 60 mg/dl of calcium in the urine;
about 110 to about 250 mmol/L of chloride in the urine;
about 25 to about 125mE/L of potassium in the urine; or
about 20 mmol/L to about 40 mmol/L of sodium in the urine.

16. The test strip of claim 1, wherein the analyte detection system of one reagent pad of the at least two reagent pads comprises a lateral flow system operable to detect the selected analyte.

17. The test strip of claim 16, wherein the plurality of components of the analyte detection system of any reagent pad of the at least two reagent pads comprise one of:
a protein;
an enzyme;
a hexokinase;
an antibody;
an antibody fragment;
a conjugated antibody;
a conjugated antibody fragment;
a conjugated anti-hormone antibody;
a conjugated anti-THC—COOH antibody;
a conjugated anti-albumin antibody;
a plurality of total protein conjugated antibodies;
ammonium purpurate; or
b-galactosidase, 5-bromo-4-chloro-3-indolyl-P-d-galactopyranoside, and magnesium.

18. The test strip of claim 17, wherein one of the conjugated antibody, the conjugated antibody fragment, the conjugated anti-hormone antibody, the conjugated anti-THC—COOH antibody, the conjugated anti-albumin antibody, and the plurality of total protein conjugated antibodies was conjugated with a conjugate comprising a fluorescent moiety.

19. The test strip of claim 16, wherein the plurality of components of the one reagent pad comprise a detection threshold at a level between:
about 0.1 mg/dl to about 20 mg/dL of the sucrose in the urine;
about 0.1 mg/dL to about 15 mg/dL of the glucose in the urine;
about 0.1 mg/dl to about 20 mg/dL of the fructose in the urine;
about 1 mg/dl to about 25 mg/dL of total protein in the urine;
about 0.1 mg/dL to about 6 mg/dL of albumin in the urine;
about 20 mg/dl to about 60 mg/dL of calcium in the urine;
about 110 to about 250 mmol/L of chloride in the urine;

about 25 to about 125mE/L of potassium in the urine; or about 20 mmol/L to about 40 mmol/L of sodium in the urine.

20. The test strip of claim 1, wherein the analyte detection system of the one reagent pad comprises a continuous-data lateral flow system operable to detect a continuous concentration range of the selected analyte.

21. The test strip of claim 20, wherein the plurality of components of the one reagent pad comprise a variable component that is immobilized on the substrate of the one reagent pad at a continuous plurality of different amounts.

22. The test strip of claim 21, wherein the variable component is printed or nanoprinted on the substrate of the one reagent pad.

23. The test strip of claim 22, wherein the continuous plurality of different amounts provide a discrimination of at least three concentrations of the analyte.

24. The test strip of claim 23, wherein the variable component provides an accuracy of less than about 10%.

25. The test strip of claim 24, wherein the variable component comprises one of a protein, an enzyme, and a hexokinase.

26. The test strip of claim 25, wherein the protein is an antibody or an antibody fragment that was conjugated with a conjugate to provide a conjugated antibody or a conjugated antibody fragment.

27. The test strip of claim 26, wherein the conjugated antibody or the conjugated antibody fragment is one of a conjugated anti-hormone antibody, a conjugated anti-THC—COOH antibody, a conjugated anti-albumin antibody, and a plurality of total protein conjugated antibodies.

28. The test strip of claim 26, wherein the conjugate is a fluorescent moiety.

29. The test strip of claim 21, wherein the plurality of components of the one reagent pad are operable to detect between:
about 0.1 mg/dl to about 20 mg/dl of the sucrose in the urine;
about 0.1 mg/dl to about 15 mg/dL of the glucose in the urine;
about 0.1 mg/dl to about 20 mg/dL of fructose in the urine;
about 1 mg/dL to about 25 mg/dL of total protein in the urine;
about 0.1 mg/dl to about 6 mg/dL of albumin in the urine;
about 20 mg/dL to about 60 mg/dl of calcium in the urine;
about 110 to about 250 mmol/L of chloride in the urine;
about 25 to about 125mE/L of potassium in the urine; or
about 20 mmol/L to about 40 mmol/L of sodium in the urine.

30. A test strip for urinalysis, the test strip comprising:
colorimetric reagent pads for detecting concentrations of different analytes in urine;
each reagent pad of the colorimetric reagent pads being attached to the test strip and comprising a substrate and an analyte detection system;
each analyte detection system comprising a plurality of components operable to detect a selected analyte of the different analytes in the urine with a resolution of at least three concentrations of the selected analyte in the urine;
wherein the different analytes comprise sucrose, glucose, and fructose; and
wherein the reagent pads comprise:
a first reagent pad comprising an analyte detection system for sucrose that detects the sucrose and the glucose in the urine and has a detection range of about 0.1 mg/dl to about 20 mg/dl of the sucrose in the urine;
a second reagent pad comprising an analyte detection system for glucose that detects the glucose in the urine and has a detection range of about 0.1 mg/dl to about 15 mg/dl of the glucose in the urine; and
a third reagent pad comprising the analyte detection system for fructose that detects the fructose in the urine and has a detection range of about 0.1 mg/dL to about 20 mg/dL of the fructose in the urine.

31. The test strip of claim 30, wherein the analyte detection system for sucrose comprises a first plurality of components comprising beta-fructosidase, glucose oxidase, and peroxidase.

32. The test strip of claim 30, wherein the plurality of components of one reagent pad of the at least two reagent pads comprise a detection range of:
about 1 mg/dl to about 25 mg/dL of total protein in the urine;
about 0.1 mg/dl to about 6 mg/dl of albumin in the urine;
about 20 mg/dl to about 60 mg/dL of calcium in the urine;
about 110 to about 250 mmol/L of chloride in the urine;
about 25 to about 125mE/L of potassium in the urine; or
about 20 mmol/L to about 40 mmol/L of sodium in the urine.

33. The test strip of claim 30, wherein the plurality of components of one reagent pad of the at least two reagent pads comprise a fluorescent moiety.

* * * * *